United States Patent [19]
Johnston et al.

[11] Patent Number: 5,600,043
[45] Date of Patent: Feb. 4, 1997

[54] OXYCHLORINATION PROCESS

[75] Inventors: Victor J. Johnston, Silver Lake; Joseph A. Cowfer, Avon Lake, both of Ohio

[73] Assignee: The Geon Company, Avon Lake, Ohio

[21] Appl. No.: 411,023

[22] Filed: Mar. 27, 1995

[51] Int. Cl.⁶ .......................... C07C 17/15; C07C 17/154
[52] U.S. Cl. ........................................... 570/243; 570/245
[58] Field of Search ..................... 570/245, 243

[56] References Cited

U.S. PATENT DOCUMENTS

| | | | |
|---|---|---|---|
| 2,636,864 | 4/1953 | Pye et al. | 570/245 |
| 4,446,249 | 5/1984 | Eden. | |
| 4,740,644 | 4/1988 | Eichhorn | 570/245 |
| 4,910,354 | 3/1990 | Derleth et al. | 570/245 |
| 5,004,849 | 4/1991 | Hirschmann et al. . | |
| 5,011,808 | 4/1991 | Scott . | |
| 5,227,548 | 7/1993 | Scott | 570/245 |

FOREIGN PATENT DOCUMENTS 0278922  11/1993  European Pat. Off. .

OTHER PUBLICATIONS

Reprinted from Kirk–Othmer: "Encyclopedia of Chemical Technology", vol. 23, Third Edition, Copyright 1983 by John Wiley & Sons, Inc., pp. 865–885.

*Primary Examiner*—Alan Siegel
*Attorney, Agent, or Firm*—Miles B. Dearth; Joe A. Powell

[57] ABSTRACT

The subject invention relates to a process for oxychlorination of ethylene to produce 1,2-dichloroethane. The process comprises contacting a mixture of ethylene, oxygen or oxygen containing gas and hydrogen chloride with a fixed or fluidized catalyst composition in a reaction zone and recovering 1,2-dichloroethane from the effluents of the reaction zone.

The invention is embodied in a process for the oxychlorination of ethylene to produce 1,2-dichloroethane by contacting a mixture of ethylene, oxygen containing gas and hydrogen chloride with a catalyst composition in a reaction zone and recovering 1,2-dichloroethane from the effluents of the reaction zone the process comprising introducing ethylene, HCl and oxygen containing gas into said reaction zone in a ratio of 1.8 and 2.2 moles of HCl per mole of ethylene and from 0.5 to 1 mole of oxygen per mole of ethylene, the oxychlorination process taking place at a temperature of from 215° C. to 230° C., ethylene conversion on a weight basis is at 99% or higher and the mixture is contacted with a catalyst including a support which has deposited thereon a combination of metal chloride salts, the combination consisting essentially of from 2 to 8% copper, from 0.2 to 2% potassium and from 0.01 to 0.19% magnesium, all percentages expressed as the metals on a weight percent basis.

7 Claims, 9 Drawing Sheets

Figure 2.
(0.2% Mg)

Figure 3.
Example 3.
(0.1% Mg)

Figure 5. Example 5. (0.12% Mg)

OXYCHLORINATION PROCESS

FIELD OF THE INVENTION

The subject invention relates to the process of oxychlorination of ethylene to produce ethylene dichloride (EDC) using copper containing catalysts.

BACKGROUND OF THE INVENTION

Catalysts used in the oxychlorination process are disclosed in U.S. Pat. Nos. 3,624,170, 4,446,249, 4,740,642, and 5,011,808 and European Patent Publication no. 0255156. An example of the conditions required in catalytic oxychlorination is described in U.S. Pat. No. 3,488,398 to Harpring et al.

U.S. Pat. No. 3,264,170 discloses an oxychlorination catalyst containing copper chloride, sodium chloride and magnesium chloride. EP-0255156 discloses an oxychlorination catalyst consisting of copper chloride, magnesium chloride, sodium and/or lithium chloride. U.S. Pat. No. 4,740,642 discloses an oxychlorination catalyst comprising copper, an alkali metal salt and a rare earth metal salt.

U.S. Pat. No. 5,011,808 discloses a non-sticking oxychlorination catalyst having improved EDC selectivity, consisting essentially of copper chloride, magnesium chloride and potassium chloride. The specified metal composition in weight percents are:

Cu: 3 to 9%, preferably 4 to 8%
Mg: 0.2 to 3%, preferably 0.2 to 1.5%
K: 0.2 to 3%, preferably 0.5 to 2%.

U.S. Pat. No. 5,011,808 teaches the above specified metal content for use under a given set of conditions, or under any conditions. Comparison between the inventive combination and controls was shown under fixed conditions, i.e. the same conditions were used for each catalyst and synergistic effects were seen in the improvement in ethylene selectivity to carbon oxides and EDC selectivity over those catalysts with either Mg or K alone with copper.

Comparisons of oxychlorination catalysts at standardized conditions provide a convenient way to illustrate differences in catalyst performance, but conclusions are limited to conditions near those controlled conditions. Such results may not reflect the highest potential performance of a catalyst which may require different. conditions for different catalysts. A truer test of performance for a particular catalyst is under conditions which are optimum for that particular catalyst. Many of the key parameters in the oxychlorination of ethylene to produce EDC are inherently coupled. Arriving at conditions for maximizing one performance parameter often comes at the expense of another. For example, conversion of ethylene can be controlled to 100% and it is well understood that increasing the reaction temperature will achieve this. However under the highest ethylene conversion conditions, the purity of the EDC product is reduced as more undesirable by-products are produced. Two key performance parameters in the oxychlorination process are EDC selectivity (selectivity of ethylene to form EDC) and ethylene efficiency and are expressed as follows:

$$EDC \text{ selectivity} = \frac{\text{Moles } EDC \text{ produced}}{\text{Moles Ethylene consumed}} \times 100$$

$$\begin{aligned}\text{Ethylene} \\ \text{efficiency}\end{aligned} = \frac{EDC \text{ selectivity} \times}{\text{ethylene conversion}}$$

$$= \frac{\text{Moles } EDC \text{ produced}}{\text{Moles ethylene fed}} \times 100$$

Also, the conversion of HCl must be maintained high in the best balance because of the problems attendant in handling and neutralizing any remaining HCl in the effluent. It is important, therefore, to find that set of conditions for a given catalyst that gives the best overall performance of that catalyst.

The realities of large scale production processes play a role in restricting the desired operating conditions. For example, in the air-based oxychlorination process, the ethylene conversion must be maintained at high levels to avoid excessive losses of ethylene. This can be accomplished by increasing the temperature of operation but this leads to reduced crude product purity and possibly reduced HCl conversion if the operating conditions are in a region beyond the maximum HCl conversion, which is likely. Specifically, the best balance of reaction conditions found for an oxychlorination catalyst are where the selectivity of ethylene conversion to EDC (EDC selectivity) is highest, breakthrough of unconverted feed lowest, and the percentage of by-product formation is lowest.

It has been found that as reaction bed temperatures increase, ethylene conversion increases to a maximum of 100% but a point of maximum HCl conversion is reached, beyond which HCl conversion decreases. Optimum conditions, unique to any oxychlorination catalyst are found at a point where ethylene conversion is at or above 99% and at a point where HCl conversion has not dropped severely. Near these conditions, the ethylene selectivity to EDC and HCl selectivity to EDC between different catalysts can be compared to arrive at conclusions as to which catalyst gives the better overall performance, compared to the other catalysts.

Another important commercial consideration pertains to the quality of fluidization. Even after an oxychlorination catalyst can be identified as having higher potential. performance than another, whether the improvement in the use of this catalyst in a commercial scale process can be realized depends on whether there is increased risk of that catalyst exhibiting stickiness in the selected operating range. If stickiness occurs, one can not safely operate in that range of conditions.

The inventors undertook a study of an oxychlorination reaction using the catalyst bed containing fluidized particles of a catalyst composition taught in U.S. Pat. No. 5,011,808. A catalyst, consisting of alumina on which was deposited 5% Cu, 0.5% K and 1.1% Mg, was employed in a series of experiments utilizing a fluid bed oxychlorination reactor. The optimum conditions were determined at a feed ratio of HCl to ethylene of 1.979, a bed temperature of from 220° C. to 230° C. and contact time of 25–26 seconds. Table C1 illustrates three of the experiments nearest the optimum. It can be seen that above 225° C., all of the parameters evidence a decline in performance. At 225° C., ethylene efficiency has peaked and HCl conversion is on a downward trend. The point nearest the optimum performance for this catalyst is at about a 225° C. bed temperature.

U.S. Pat. No. 5,011,808 specifies a minimum magnesium content of 0.2% on a metal weight basis. A catalyst containing 5% CU, 0.5%k and 0.2% Mg was tested under a series of continuous oxychlorination reactions. Those conditions nearest the optimum performance are listed in Table C2. The key performance parameters measured, HCl conversion, ethylene efficiency, crude purity and percent 1,1,2-trichloroethane (by-product) are shown.

TABLE C1

| Temp °C. | HCl Conversion | Ethylene Efficiency | Crude Purity | By-Product 1,1,2 |
|---|---|---|---|---|
| 220 | 99.18% | 96.58% | 99.59% | 0.32% |
| 225 | 98.27 | 97.48 | 99.44 | 0.45 |
| 230 | 98.19 | 97.20 | 99.23 | 0.62 |

TABLE C2

| Temp °C. | HCl Conversion | Ethylene Efficiency | Crude %% Purity | By-Product 1,1,2 |
|---|---|---|---|---|
| 210 | 98.8% | 96.74% | 99.67% | 0.23% |
| 215 | 98.75 | 96.8 | 99.47 | 0.33 |
| 220 | 98.61 | 96.3 | 99.34 | 0.43 |

It is evident from tables C1 and C2 that as the magnesium content was reduced from 1% to 0.2% on a metal weight basis, the maximum obtainable ethylene efficiency dropped from 97.48% to 96.8%. One would suspect that at this reduced level of magnesium, that the synergistic interaction with potassium and magnesium was abating in view of U.S. Pat. No. 5,011,808. Further study of optimized performance of other catalysts at lower magnesium levels lead to an unexpected observance, which on a commercial scale will provide a significant improvement in the oxychlorination process. A commercial scale increase in ethylene efficiency of 0.5% can translate into a savings on the order of $200–500,000 annually.

SUMMARY OF THE INVENTION

The invention is embodied in a process for the oxychlorination of ethylene to produce 1,2-dichloroethane by contacting a reaction mixture of ethylene, oxygen or an oxygen containing gas and hydrogen chloride with a catalyst in a fixed bed or fluidized bed reaction zone, and recovering 1,2-dichloroethane from the effluents, the process comprising introducing ethylene, HCl and oxygen containing gas into said reaction zone in a ratio of 1.8 and 2.2 moles of HCl per mole of ethylene and from 0.5 to 1 mole of oxygen per mole of ethylene, at a temperature of from 210° C. to 250° C., the reaction mixture is contacted with a catalyst having a support on which is deposited thereon a combination of active metals, the combination, expressed in terms of the chloride salts consist essentially of from 4 to 17% by weight copper chloride, from 0.37 to 3.8% by weight potassium chloride and from 0.04 to 75% by weight magnesium chloride. Expressed on an atomic metal weight basis the catalyst consists essentially of from 2% to 8% copper, from 0.2 to 2% potassium and from 0.01 to 0.19% magnesium on the support.

The catalyst compositions are prepared by depositing the active metals on the support. The process of the present invention yields unexpectedly higher percent ethylene efficiency, higher EDC product purity and higher percent HCl conversion. Also unexpectedly under the optimum performance conditions, catalyst stickiness does not occur.

DETAILED DESCRIPTION OF THE INVENTION

Support materials upon which the metals are deposited are readily fluidizable, relatively stable, mechanically strong and resistant to attrition. Examples of support materials include but are not limited to materials such as silica, magnesia, kieselguhr, clay, fuller's earth, alumina or combinations thereof. The preferred supports are high surface area aluminas (often referred to as γ-alumina). The invention will be described hereinafter in terms of fluidizable alumina embodiments as illustrative and not limitative.

The copper metal is preferably introduced in the form of a water soluble salt, such as cupric chloride, the nitrate salt, carbonate salt or other halide salts like the bromide salt. The amount of copper on a metal basis employed is in the general range from 2% by weight to 8% by weight, or, from 4% to 17% by weight on the basis of copper (II) chloride salt, both based on the total weight of the catalyst composition. The preferred copper salt is copper chloride. The most preferred maximum amount of copper metal is about 5.0% by weight based on the total weight of the catalyst.

Potassium chloride is the preferred form for introducing potassium metal to the support. Other forms such as the carbonate salt or other halide salts like the bromide salt could be used. Potassium metal is present in the range from 0.2% to 2.0% by weight based on the total weight of the catalyst composition. More preferably 0.25% and most preferably 0.5% minimum potassium metal is present.

Magnesium metal is present at from 0.01% to less than 0.2% (0.19%) by weight based on the total weight of the catalyst. The most preferred minimum amount of magnesium is 0.05 and the preferred maximum amount of magnesium metal is 0.15% by weight based on the total weight of the catalyst.

The metal salts can be added onto the support by addition of a solution of the salt in any suitable solvent. While any metal salts capable of forming a solution are suitable, the preferred metal salts are the chloride salts. The preferred solvent is water.

The generally accepted method of addition of the metals onto the support is accomplished by impregnating the support with an aqueous solution of water soluble salts of the metals then drying the wetted support under heat. An amount of the metal salt is chosen so that the final catalyst contains the above specified ranges of copper, potassium, and magnesium.

The surface area and pore volume of the support material is modified by reason of the deposition of the metal salts. Hence, the fluidizable or fixed type catalysts have a surface area after preparation in the range of about 20 to about 220 m$^2$/g, which is about 10% to 30% lower than the surface area of the support before deposition of the metals. The preferred range of surface area for treated fluidizable bed catalysts is about 70 to about 170 m$^2$/g. The most preferred range of surface area for fluidizable catalysts is from about 80 to about 150 m$^2$/g.

By "consisting essentially of" it is meant that the active metal mixture either contains no other added metals or only contains other metals in an amount which will have no material effect on the performance of the catalyst. For example, there may be tramp levels of transition metals such as iron, zinc, lead, and the like which are or become incorporated in the catalyst support along with the active metal composition. It is recognized that some alumina support materials may contain in addition to aluminum oxide ($Al_2O_3$) very small amounts of other metal oxides like sodium oxide, magnesium oxide, etc. These alumina supports are readily useable in this invention.

The process comprises contacting ethylene, oxygen or an oxygen containing gas and hydrogen chloride (HCl) with the catalyst described herein in a reaction zone and recovering the effluent of the reaction zone. This process can be carried out as a once-through mode wherein any unreacted ethylene is vented through an incinerator or otherwise removed, or in a recycle process wherein the unreacted ethylene is recycled back into the reactor.

In the recycle mode lower ethylene conversion is not problematic since the unconverted ethylene is recycled and passed again through the oxychlorination reactor. Advantages of the recycle process include (1) lower conversion of ethylene; in general ethylene conversion is inversely related to selectivity, therefore decreased ethylene conversion (per pass<99.0%) can result in improved selectivity, and (2) improved safety since levels of oxygen in the vent/recycle gas can be independently controlled and maintained outside the explosive envelope.

In the once through process, unconverted ethylene is subsequently burned in a vent gas incinerator. Since ethylene efficiency (EE) is the product of EDC selectivity and ethylene conversion:

$$EE = EDC\ Sel \times C_2H_4\ Conv. = \frac{\text{Mole } EDC \text{ Produced}}{\text{Mole } C_2H_4\ Rxtd} \times \frac{\text{Mole } C_2H_4\ Rxtd}{\text{Mole } C_2H_4\ Fed}$$

$$= \frac{\text{Mole } EDC \text{ Produced}}{\text{Mole } C_2H4\ Fed.}$$

it follows that ethylene efficiency is a better measure of overall performance for the once-through processes. Therefore, for once-through processes it is desirable to obtain the highest level of ethylene efficiency while for recycle processes it is desirable to obtain the highest level of EDC selectivity.

In recycle processes only a small fraction of the recycle gas is vented so most of the unconverted ethylene is recycled back to the reactor. In this case, the net overall conversion of ethylene is generally >99.9%. In practice, recycle processes typically are operated at slightly lower temperatures and slightly lower $HCl/C_2H_4$ ratios. Per pass conversion is sometime kept quite low (<99%), depending on whether the recycle gas is oxygen lean or oxygen rich.

Contact times in fluid bed and fixed bed catalysis may be controlled in a range of from about 10 seconds to about 50 seconds. Contact time is defined as the ratio of reactor volume taken up by the catalyst to the volumetric flow rate of the feed gases at the reactor control temperature and top pressure. Most preferably, contact time is from about 20 to 35 seconds.

The specific Examples set forth below illustrate the unique and unexpected characteristics of the discovery. The Examples particularly point out the improvement using a combination of copper, potassium and magnesium in the specified amounts under the specified conditions. In all of the Examples, the fluid bed oxychlorination reaction is conducted using a glass laboratory fluid bed reactor. The reactor volume, the amount of catalyst charged to the reactor, the fluid density, the reactant flow rates, the temperature and the pressure all affect the contact time between reactants and catalyst. Reactor height to diameter ratio can also effect reaction conversions, selectivities, and efficiencies. These parameters were held constant in order to isolate true differences in performance of the catalyst at the optimum conditions.

In general, an oxychlorination reactor is equipped with means for delivering gaseous ethylene, oxygen or air, and HCl to the reaction zone, means for controlling the quantities of reactants and reaction conditions, and means for measuring and ascertaining the composition of the effluent gases to determine the results of the process, including but not limited to, percent HCl conversion, percent yield of EDC, and percent ethylene efficiency and EDC product purity. A detailed discussion of the oxychlorination process is given in a review article entitled *Vinyl Chloride* by J. A. Cowfer and A. J. Magistro, Kirk-Othmer: Encyclopedia of Chemical Technology, Vol. 23 3rd ed., 1983, John Wiley and Sons, Inc., pp 865–885 which are hereby incorporated by reference.

The preferred catalytic process is the fluid bed process using a fluidizable high surface area catalyst described above herein and the invention, for simplicity and convenience, will be exemplified by fluid bed catalysts, it being understood that this is merely intended in an illustrative sense and not limitative as the process is also superior in a fixed bed configuration.

EXAMPLES

Preliminary fluid bed oxychlorination runs were conducted over a range of temperatures for each catalyst. Two controls (1 and 2) and three inventive examples are shown. Controls 1 and 2 are examples of catalysts described in U.S. Pat. No. 5,011,808. Within the range of temperatures employed for each catalyst, the best performance was observed by evaluating the best balance of ethylene efficiency, HCl conversion, the selectivities toward making EDC, and the level of purity of EDC. The catalyst Control-1 contained the following active metal composition on a weight basis:

| Control-1 Metal Content % by weight | |
|---|---|
| copper | 5.0 weight % |
| potassium | 0.5 weight % |
| magnesium | 1.1 weight % |

Figure 1:
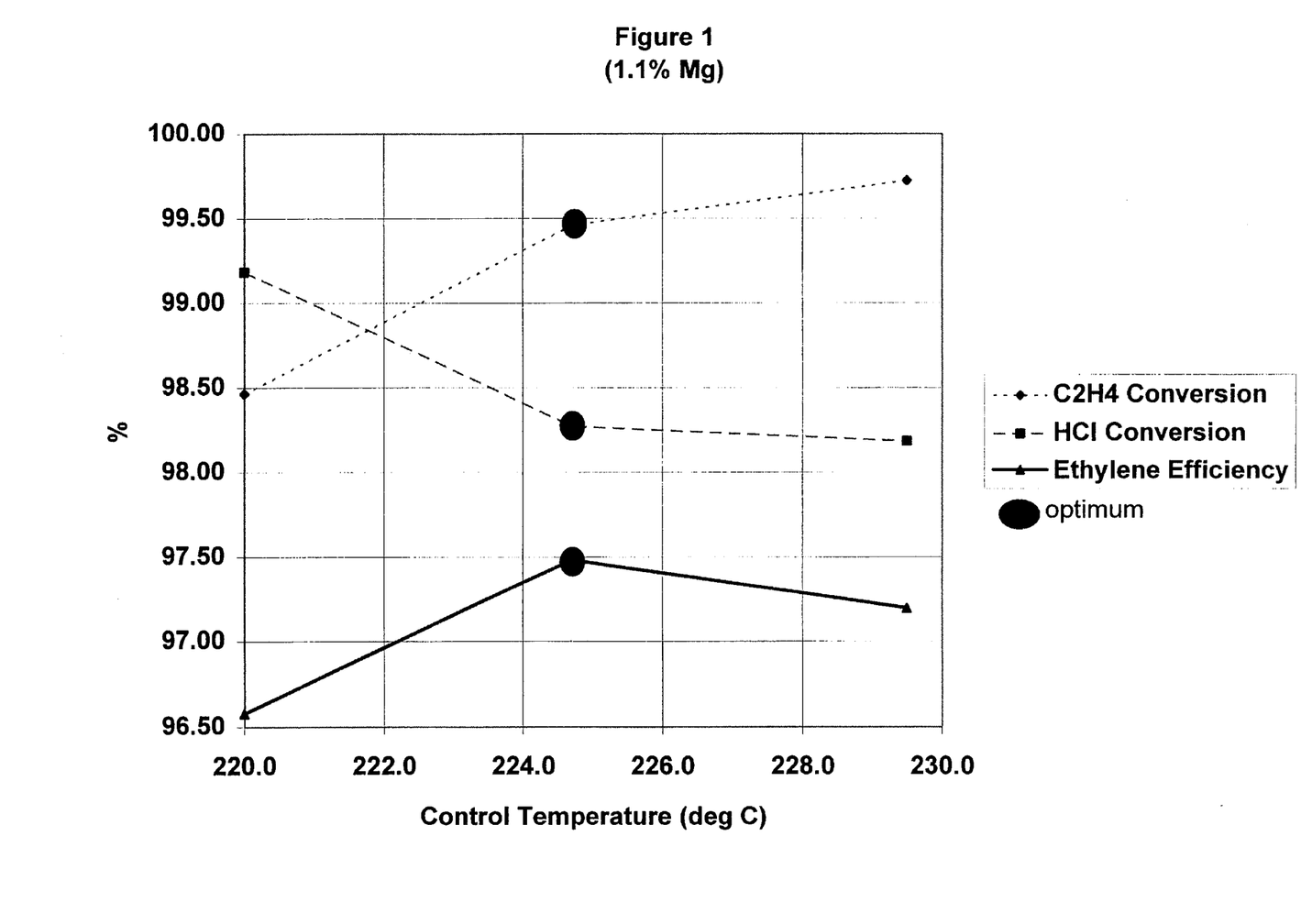
FIG. 1–5 are plots of ethylene conversion, HCl coversion and ethylene efficiency on the y-axis versus temperature of the oxychlorination process for Control-1, Control-2, Examples 3, 4, and 5, respectively.

A series of nine experiments were run and the process conditions are illustrated in Table 1. The performance measurements in each experiment are tabulated in Table 2. FIG. 1 is a graphical representation of three experimental runs found to give performance nearest the optimum for this process and catalyst, namely experiments 4, 5, and 6. FIG. 1 illustrates that the optimum performance is near 225° C. because firstly ethylene conversion needs to be at least 99% for extrapolating to commercial conditions from a lab reactor, and HCl conversion must be balanced with ethylene efficiency. The best point will be reached where ethylene conversion is closest to 99% and where HCl conversion has not dropped too severely. In the region of 99+% ethylene conversion, it has been found that HCl conversion is usually inversely proportional to ethylene conversion, that is, at a point beyond where HCl conversion is maximum.

TABLE 1

| | | CONTROL-1 | | | | | |
|---|---|---|---|---|---|---|---|
| EXPERIMENT | CONTROL TEMP (°C.) | HCl C2H4 RATIO | C2H4[1] CNV (%) | HCl[2] CNV (%) | C2H4[3] EFF (%) | HCl[4] EFF (%) | EDC[5] PURITY (WT %) |
| #3- | 219.3 | 1.949 | 98.22 | 99.21 | 96.21 | 98.74 | 99.58 |
| #1- | 224.5 | 1.946 | 98.89 | 99.33 | 95.93 | 98.60 | 99.38 |
| #2- | 229.6 | 1.947 | 99.41 | 99.33 | 95.66 | 98.29 | 99.10 |
| #6- | 220.0 | 1.997 | 98.46 | 99.18 | 96.58 | 98.72 | 99.59 |
| #5- | 224.7 | 1.997 | 99.46 | 98.27 | 97.48 | 97.65 | 99.44 |
| #4- | 229.5 | 1.997 | 99.72 | 98.19 | 97.20 | 97.33 | 99.23 |
| #7- | 230.2 | 1.886 | 98.21 | 99.40 | 91.61 | 97.16 | 98.18 |
| #8- | 234.7 | 1.895 | 99.07 | 99.50 | 91.78 | 96.86 | 97.84 |
| #9- | 239.5 | 1.897 | 99.54 | 99.40 | 91.19 | 96.13 | 97.32 |

Hereinafter:
[1]C2H4 cnv = % ethylene conversion
[2]HCl cnv = % HCl conversion
[3]C2H4 eff = ethylene efficiency (%)
[4]HCl eff = HCl efficiency %
[5]EDC = ethylene dichloride The following catalyst was used under conditions similar to control-1:

| Control-2 % by weight | |
|---|---|
| copper | 5.0 weight % |
| potassium | 0.5 weight % |
| magnesium | 0.2 weight % |

Figure 2:
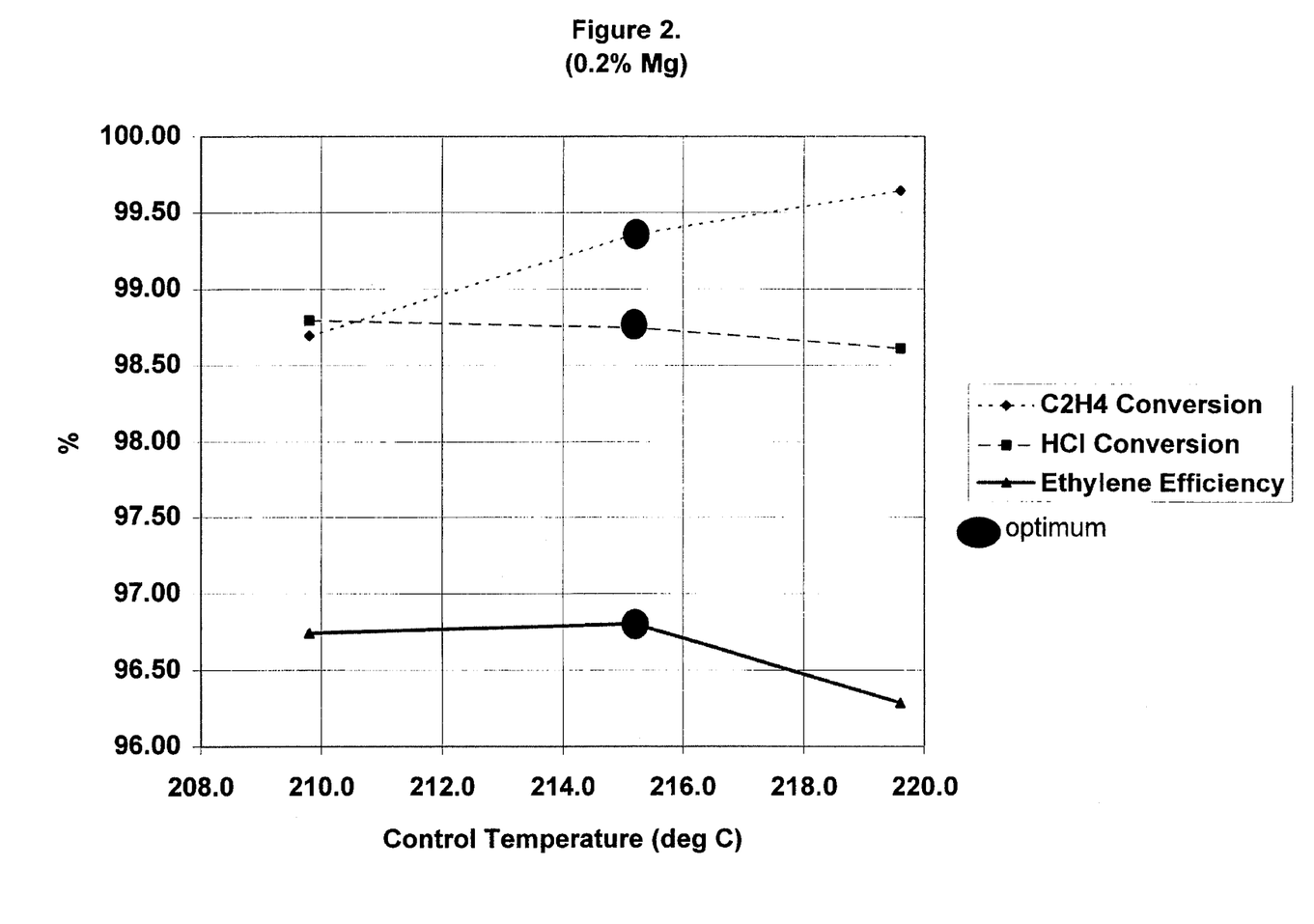

FIG. 2 illustrates graphically the three experiments nearest where the true optimum performance for Control-2 is obtainable. From the graph, it can be seen that the optimum performance for the process using Control-2 is experiment No. 6 run at 215° C. Under these conditions, ethylene efficiency is highest and HCl conversion is not significantly below its maximum. Below this optimum range, ethylene efficiency is significantly lower.

TABLE 2

| | | | Control-2 | | | | | |
|---|---|---|---|---|---|---|---|---|
| EXPERIMENT | CONTROL TEMP (°C.) | HCl C2H4 RATIO | CONTACT TIME (SEC) | C2H4[1] CNV (%) | HCl[2] CNV (%) | C2H4[3] EFF (%) | HCl[4] EFF (%) | EDC[5] PURITY (WT %) |
| #3- | 210 | 1.921 | 26 | 97.51 | 99.22 | 94.87 | 98.77 | 99.59 |
| #2- | 215 | 1.934 | 26 | 98.98 | 99.22 | 95.35 | 98.59 | 99.45 |
| #1- | 221 | 1.933 | 26 | 99.36 | 99.16 | 94.97 | 98.28 | 99.23 |
| #6- | 210 | 1.966 | 26 | 98.70 | 98.80 | 96.74 | 98.43 | 99.67 |
| #5- | 215 | 1.972 | 26 | 99.36 | 98.75 | 96.80 | 98.18 | 99.47 |
| #4- | 220 | 1.968 | 26 | 99.64 | 98.61 | 96.29 | 97.86 | 99.34 |
| #7- | 220 | 1.887 | 26 | 98.47 | 99.44 | 92.60 | 98.17 | 98.95 |
| #9- | 225 | 1.891 | 25 | 99.16 | 99.39 | 92.39 | 97.72 | 98.62 |
| #8- | 230 | 1.896 | 25 | 99.70 | 99.31 | 92.23 | 97.27 | 98.29 |

TABLE 3

| EXPERIMENT NUMBER | CONTROL TEMP (°C.) | HCl C2H4 RATIO | CONTACT TIME (sec) | C2H4 cnv (%) | HCl cnv (%) | C2H4 eff (%) | HCl eff (%) | EDC PURITY (wt %) |
|---|---|---|---|---|---|---|---|---|
| #3- | 214.4 | 1.949 | 25.696 | 98.61 | 99.18 | 96.23 | 98.72 | 99.60 |
| #2- | 220.0 | 1.936 | 25.408 | 99.05 | 99.14 | 95.21 | 98.34 | 99.32 |
| #1- | 225.2 | 1.943 | 25.145 | 99.56 | 98.86 | 95.04 | 97.83 | 99.11 |
| #6- | 214.7 | 1.999 | 25.803 | 98.30 | 97.44 | 97.10 | 97.14 | 99.71 |
| #5- | 219.4 | 1.991 | 25.558 | 99.13 | 98.55 | 97.74 | 98.20 | 99.67 |
| #4- | 224.4 | 2.011 | 25.299 | 99.60 | 97.58 | 97.61 | 97.05 | 99.50 |
| #8- | 220.2 | 1.907 | 25.293 | 98.39 | 99.31 | 93.77 | 98.33 | 99.19 |
| #7- | 224.6 | 1.917 | 25.070 | 99.08 | 99.31 | 93.55 | 97.59 | 98.59 |
| #9- | 230.1 | 1.919 | 24.795 | 99.44 | 99.27 | 93.09 | 97.03 | 98.17 |

Example 3 active metal content (wt %)
Cu - 5%
K - 0.46%
Mg - 0.10%

TABLE 4

| EXPERIMENT NUMBER | CONTROL TEMP (°C.) | HCl C2H4 RATIO | CONTACT TIME (sec) | C2H4 cnv (%) | HCl cnv (%) | C2H4 eff (%) | HCl eff (%) | EDC PURITY (wt %) |
|---|---|---|---|---|---|---|---|---|
| #3- | 214.9 | 1.938 | 25.766 | 98.82 | 99.09 | 95.51 | 98.56 | 99.54 |
| #2- | 221.0 | 1.947 | 25.488 | 99.53 | 98.94 | 95.63 | 98.22 | 99.37 |
| #1- | 225.0 | 1.951 | 25.243 | 99.73 | 98.11 | 94.69 | 97.09 | 99.11 |
| #6- | 215.0 | 1.985 | 25.861 | 99.16 | 98.77 | 97.72 | 98.46 | 99.74 |
| #5- | 220.0 | 1.981 | 25.599 | 99.47 | 98.84 | 97.53 | 98.48 | 99.67 |
| #4- | 225.0 | 1.994 | 25.342 | 99.86 | 97.48 | 96.33 | 96.61 | 99.22 |
| #7- | 225.0 | 1.890 | 25.138 | 98/93 | 99.40 | 92.08 | 97.44 | 98.40 |
| #8- | 230.0 | 1.891 | 24.88 | 99.55 | 99.42 | 91.64 | 96.91 | 97.94 |
| #9- | 235.0 | 1.906 | 24.643 | 99.90 | 99.10 | 91.77 | 96.29 | 97.68 |

Example 4 active metal content (wt %)
Cu - 5%
K - 0.5%
Mg - 0.10%

TABLE 5

| EXPERIMENT NUMBER | CONTROL TEMP (°C.) | HCl C2H4 RATIO | CONTACT TIME (sec) | C2H4 cnv (%) | HCl cnv (%) | C2H4 eff (%) | HCl eff (%) | EDC PURITY (wt %) |
|---|---|---|---|---|---|---|---|---|
| #3- | 210.0 | 1.946 | 25.938 | 98.38 | 99.08 | 95.56 | 98.21 | 99.26 |
| #2- | 214.7 | 1.949 | 25.689 | 99.09 | 98.99 | 95.43 | 97.93 | 99.12 |
| #1- | 220.2 | 1.947 | 25.403 | 99.53 | 98.89 | 95.02 | 97.62 | 98.93 |
| #6- | 201.9 | 1.993 | 26.484 | 98.23 | 98.05 | 96.63 | 97.62 | 98.93 |
| #5- | 213.4 | 1.993 | 25.857 | 99.57 | 98.54 | 97.26 | 97.76 | 99.33 |
| #4- | 219.5 | 1.993 | 25.537 | 99.76 | 98.50 | 97.19 | 97.55 | 99.18 |
| #7- | 220.3 | 1.909 | 25.292 | 98.68 | 99.30 | 92.80 | 97.23 | 98.31 |
| #8- | 225.0 | 1.918 | 25.052 | 99.26 | 99.03 | 92.65 | 96.60 | 98.02 |
| #9- | 230.1 | 1.898 | 24.785 | 98.51 | 98.62 | 91.60 | 96.53 | 98.28 |

Example 5 active metal content (wt %)
Cu - 5.19%
K - 0.45%
Mg - 0.12%

Discussion

Figure 3:
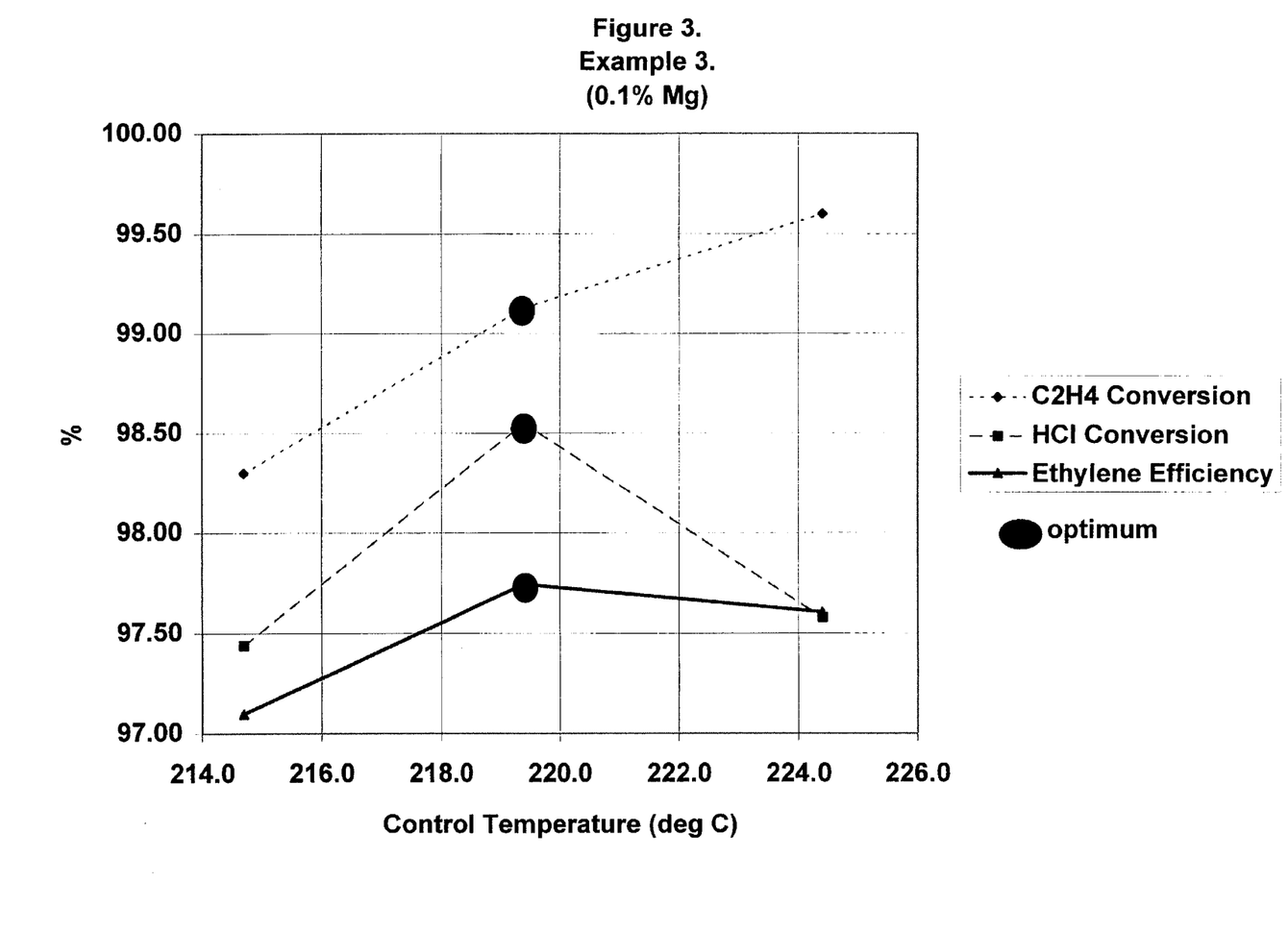
Figure 4:
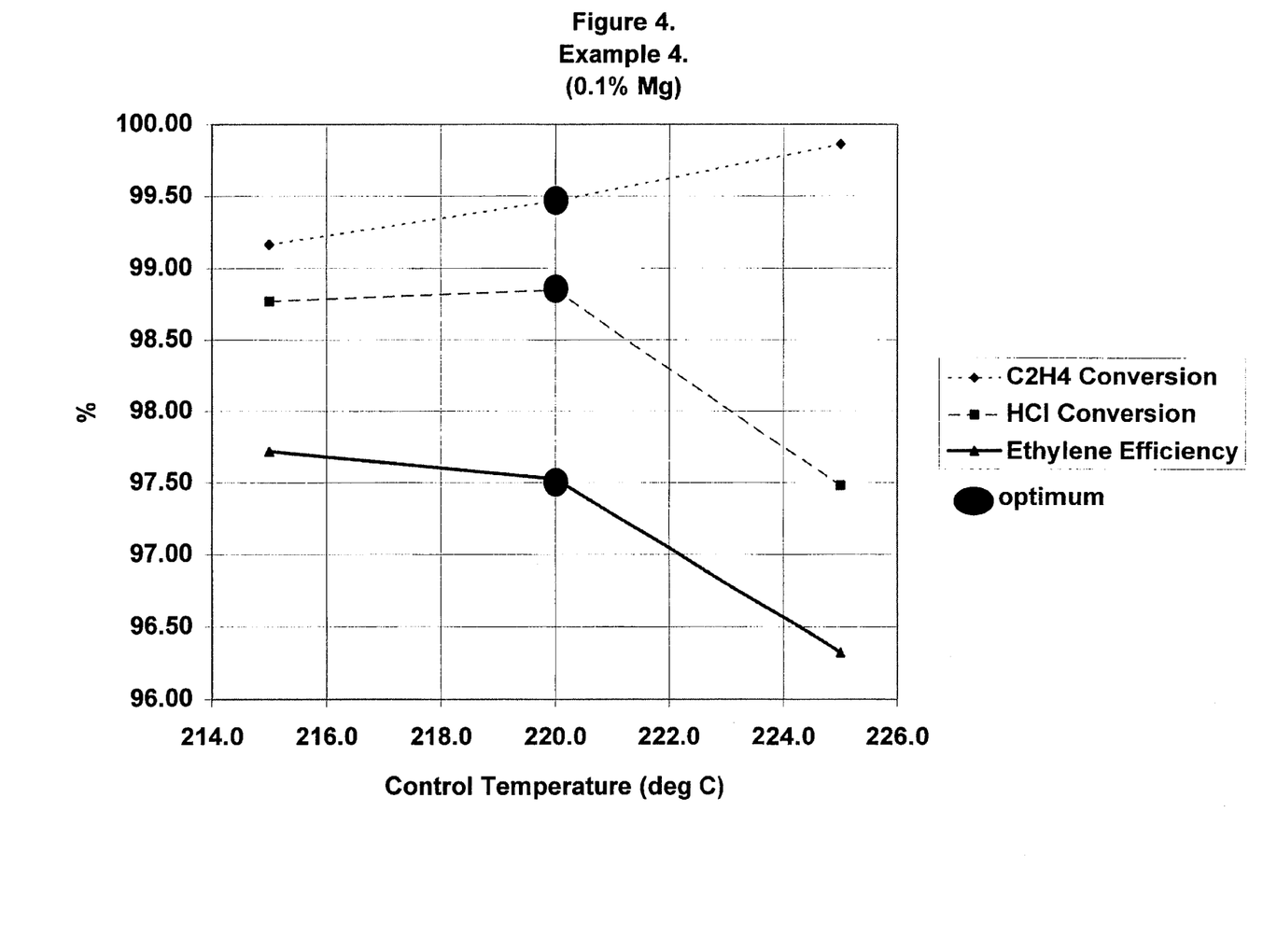
Figure 5:
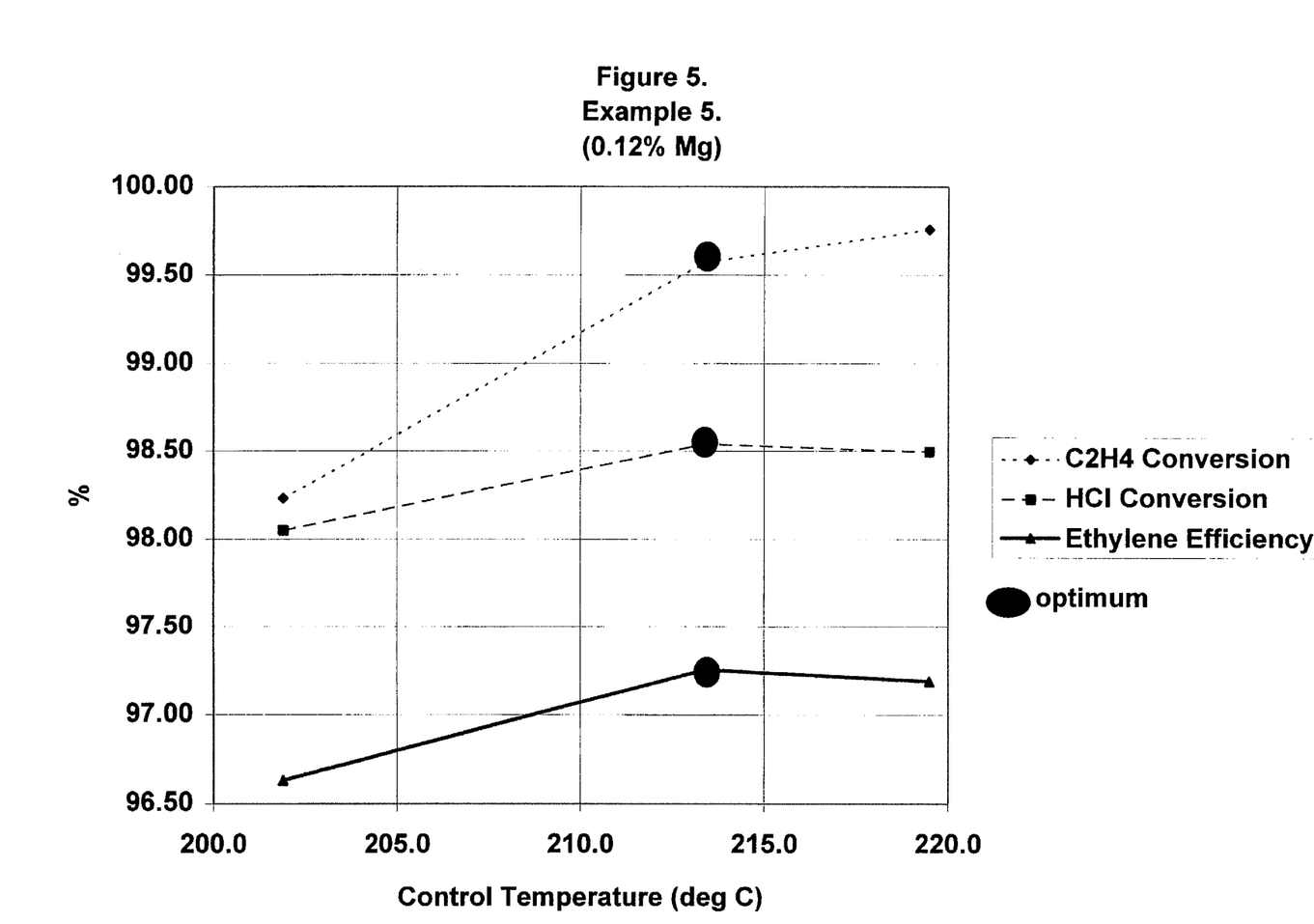

With the results of each of the series of oxychlorination runs under conditions within which the maximum balance of performance occurs with each catalyst, several significant differences were appreciated. From tables 3, 4, and 5, the best performance obtained in the process was in a temperature range of from 215° C. to 220° C. FIGS. 3, 4, and 5 illustrate where the optimums occur. In the use of a catalyst consisting of Cu, K and Mg, it was surprising to discover that better results were obtained when the Mg level was below 0.2% than when the Mg level was at 0.2%, considering that the prior art showed catalyst performance declining as the Mg content was decreased from 1.1 to 0.2%. The most preferred catalyst is example 5 where Mg is at 0.12% by weight. Here, unexpectedly, it is found that ethylene conversion can be pushed to 99.76% without a significant drop in HCl conversion (~98.5%) or ethylene efficiency (~97.2%).

Figure 6:
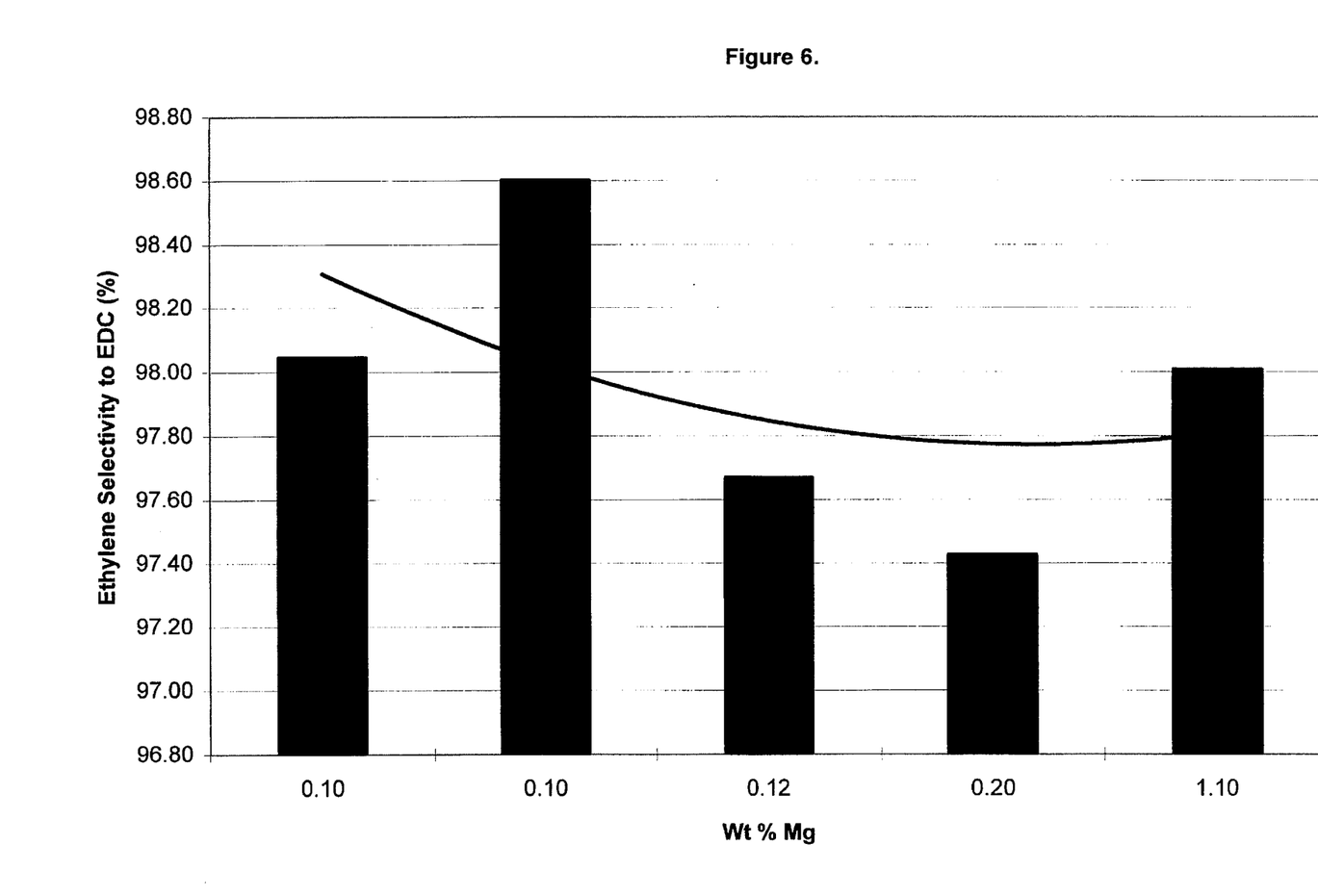
FIGS. 6, 7, 8, and 9 are plots of ethylene selectivity, amount of 1,1,2-trichloroethane, ethylene efficiency, and HCl selectivity to EDC on the y-axis as percent, versus weight percent magnesium level in the various oxychlorination catalysts containing magnesium, copper, and potassium.
Figure 7:
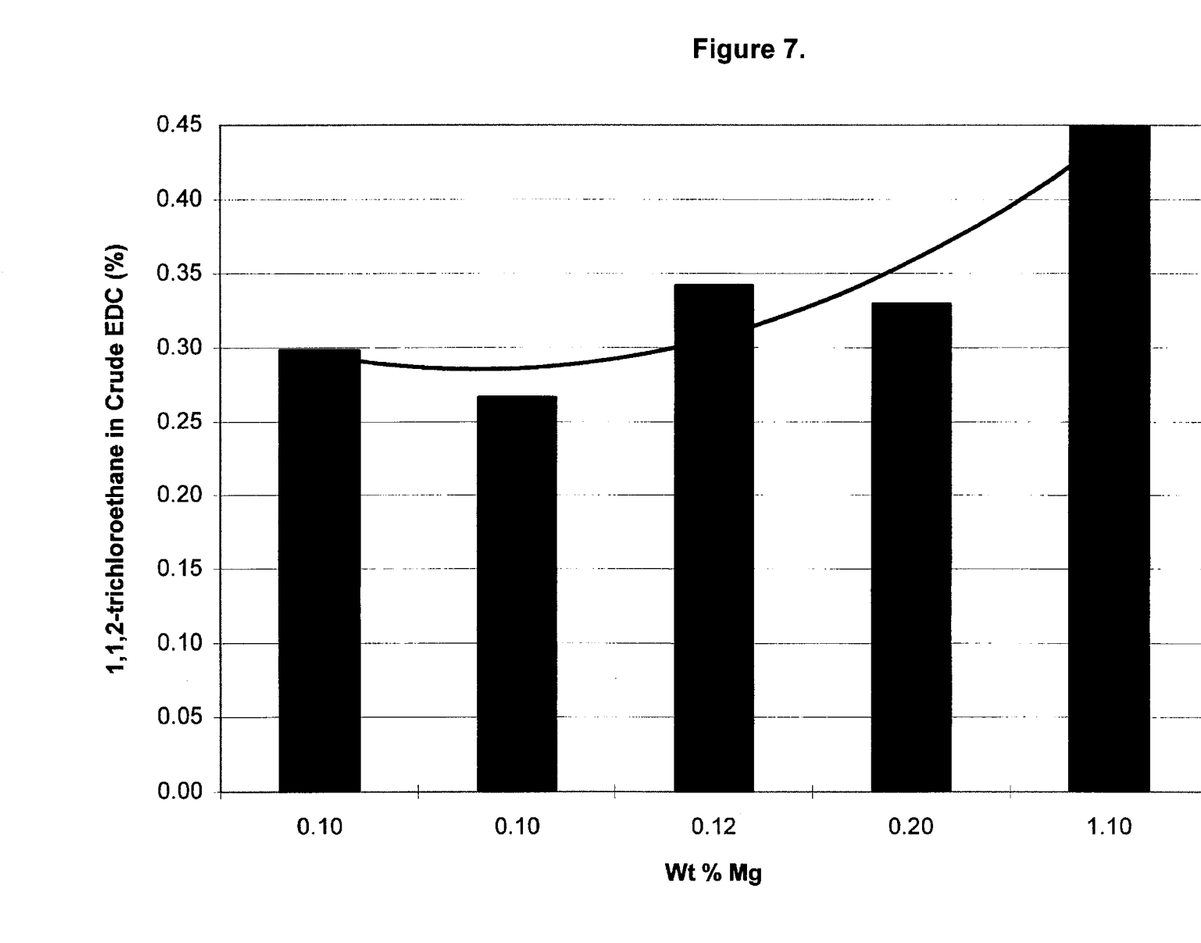
Figure 8:
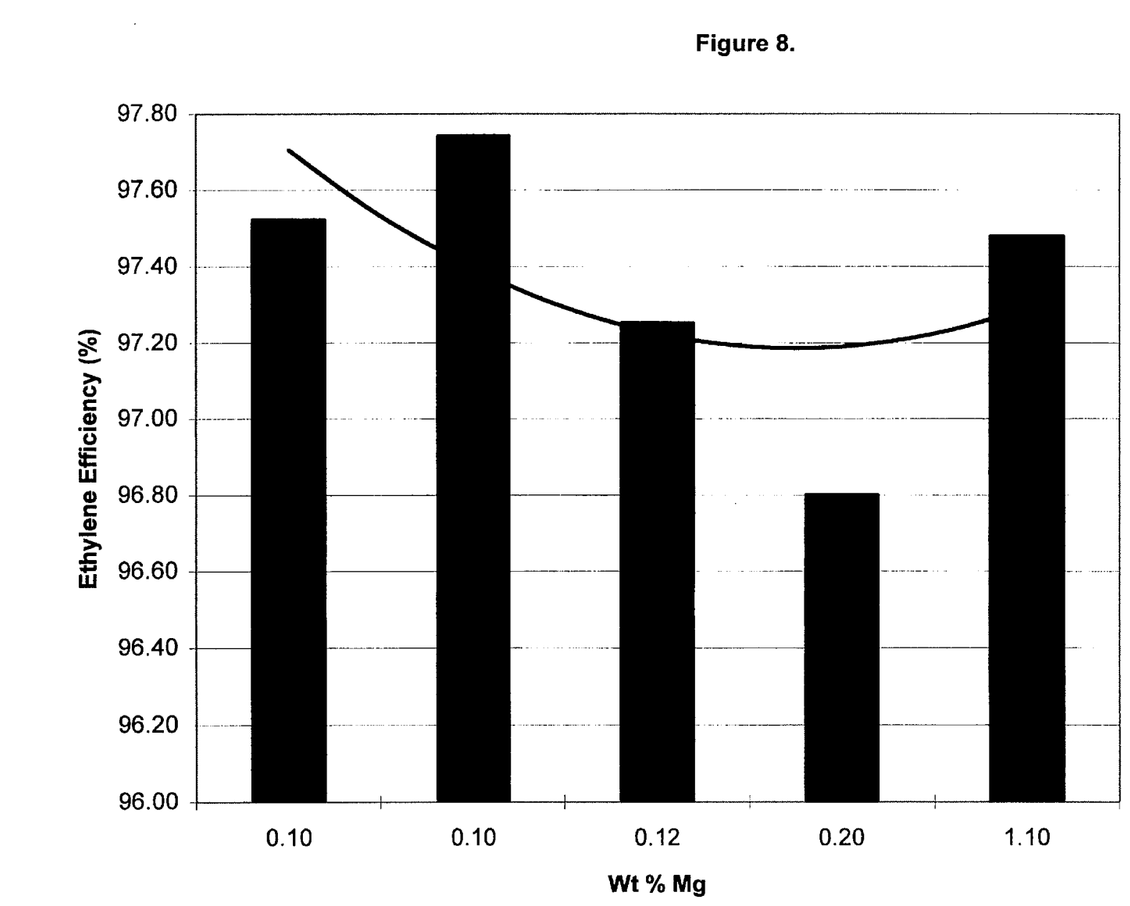
Figure 9:
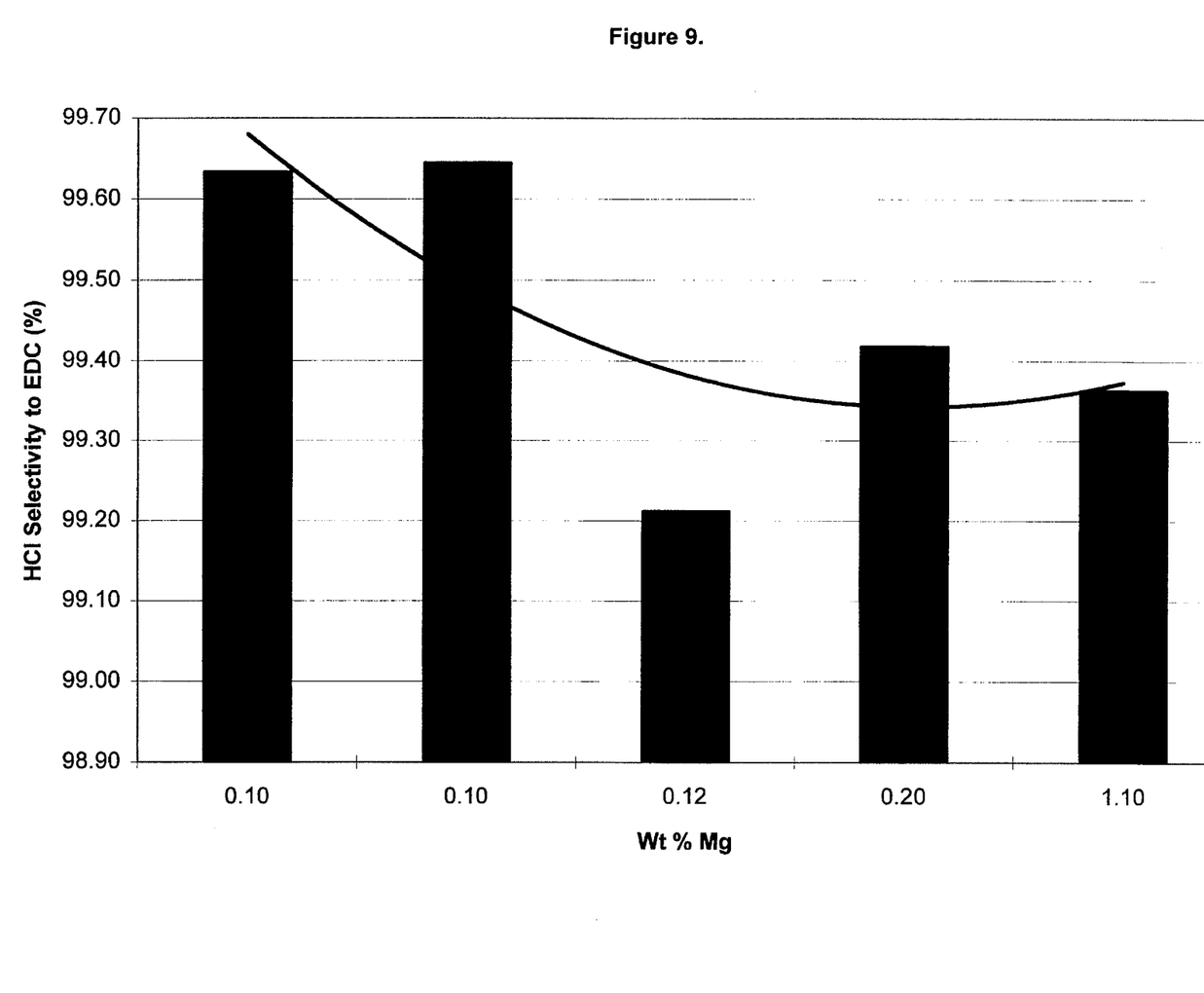

FIGS. 6–9 illustrate in stark contrast, the improved performance in the following parameters:

FIG. 6—Ethylene selectivity to EDC
FIG. 7—Level of by-product impurity
FIG. 8—Ethylene efficiency to EDC
FIG. 9—HCl selectivity to EDC.

What is claimed is:

1. A process for the oxychlorination of ethylene to produce 1,2-dichloroethane by contacting a mixture of ethylene, oxygen containing gas and hydrogen chloride with a catalyst composition in a reaction zone and recovering 1,2-dichloroethane from the effluents of the reaction zone the process comprising introducing ethylene, HCl and oxygen containing gas into said reaction zone in a ratio of 1.8 and 2.2 moles of HCl per mole of ethylene and from 0.5 to 1 mole of oxygen per mole of ethylene, the oxychlorination process taking place at a temperature of from 210° C. to 250° C., ethylene conversion on a weight basis is at 99% or higher and the mixture is contacted with a catalyst including a support which has deposited thereon a combination of metals, the combination consisting essentially of from 3% to about 6% copper metal, from 0.2% to about 1% potassium metal and from 0.05% to 0.15% magnesium metal, all percentages expressed on a weight percent basis.

2. The process of claim 1 wherein the metals are deposited on a fluidizable high surface area support.

3. The process of claim 1 wherein the metals are deposited on a support and the catalysis is carried out on a fixed bed.

4. The process of claim 2 wherein the support is an alumina support.

5. The process of claim 1 further characterized in that the ratio of ethylene, HCl, and oxygen employed range from about 1.0 to about 1.1 moles of ethylene and about 0.5 mole to about 0.9 mole of oxygen for every 2.0 moles of HCl.

6. The process of claim 1 wherein the reactants are passed over the catalyst in a once through process.

7. The process of claim 1 wherein after passing through said reaction zone unreacted ethylene is recycled back to said reaction zone.

* * * * *